(12) United States Patent
Arramon et al.

(10) Patent No.: US 11,207,190 B2
(45) Date of Patent: Dec. 28, 2021

(54) POLYARYLETHERKETONE ARTIFICIAL INTERVERTEBRAL DISC

(71) Applicant: Simplify Medical Pty Ltd., Paddington NSW (AU)

(72) Inventors: Yves Arramon, Sunnyvale, CA (US); Malan de Villiers, Wapadrand (ZA); Neville Jansen, Waterkloof (ZA)

(73) Assignee: Simplify Medical Pty Ltd, Paddington (AU)

( * ) Notice: Subject to any disclaimer, the term of this patent is extended or adjusted under 35 U.S.C. 154(b) by 0 days.

(21) Appl. No.: 15/796,086

(22) Filed: Oct. 27, 2017

(65) Prior Publication Data

US 2018/0064553 A1    Mar. 8, 2018

Related U.S. Application Data

(63) Continuation of application No. 12/435,572, filed on May 5, 2009, now abandoned.

(Continued)

(51) Int. Cl.
*A61F 2/44*    (2006.01)
*A61F 2/30*    (2006.01)
(Continued)

(52) U.S. Cl.
CPC ............ *A61F 2/4425* (2013.01); *A61L 27/18* (2013.01); *C08L 71/00* (2013.01); *A61F 2/30734* (2013.01); *A61F 2/30965* (2013.01); *A61F 2002/305* (2013.01); *A61F 2002/3008* (2013.01); *A61F 2002/30448* (2013.01); *A61F 2002/30565* (2013.01); *A61F 2002/30663* (2013.01); *A61F 2002/30841* (2013.01); *A61F 2002/30879* (2013.01); *A61F 2002/30884* (2013.01); *A61F 2002/30899* (2013.01);
(Continued)

(58) Field of Classification Search
CPC ..................................... A61F 2/4425
See application file for complete search history.

(56) References Cited

U.S. PATENT DOCUMENTS

| 3,486,505 A | 12/1969 | Gordon |
| 3,867,728 A | 2/1975 | Stubstad et al. |

(Continued)

FOREIGN PATENT DOCUMENTS

| DE | 3023353 A1 | 4/1981 |
| DE | 10035182 A1 | 2/2002 |

(Continued)

OTHER PUBLICATIONS

Buttner-Janz, The Development of the Artificial Disc. Introduction, pp. 1-18, Library of Congress Catalogue No. 92-75582, ISBN 0-9635430-0-8 (1989).

(Continued)

*Primary Examiner* — Jacqueline Woznicki
(74) *Attorney, Agent, or Firm* — Hoffman Warnick, LLC

(57) ABSTRACT

An intervertebral prosthesis for insertion between adjacent vertebrae, in one embodiment, includes upper and lower prosthesis plates and a movable core. The prosthesis plates and optionally the core are formed of polyaryletherketone (PAEK) for improved imaging properties. A metallic insert is provided on each of the PAEK prosthesis plates providing a bone ongrowth surface.

18 Claims, 11 Drawing Sheets

Related U.S. Application Data

(60) Provisional application No. 61/082,012, filed on Jul. 18, 2008, provisional application No. 61/050,455, filed on May 5, 2008.

(51) Int. Cl.
  *A61L 27/18* (2006.01)
  *C08L 71/00* (2006.01)

(52) U.S. Cl.
  CPC .............. *A61F 2002/30904* (2013.01); *A61F 2002/443* (2013.01); *A61F 2310/00407* (2013.01); *A61F 2310/00796* (2013.01); *A61L 2430/38* (2013.01)

(56) References Cited

U.S. PATENT DOCUMENTS

| | | |
|---|---|---|
| 4,309,777 A | 1/1982 | Patil |
| 4,531,917 A | 7/1985 | Linkow et al. |
| 4,566,466 A | 1/1986 | Ripple et al. |
| 4,619,660 A | 10/1986 | Christiansen et al. |
| 4,673,407 A | 6/1987 | Martin |
| 4,759,766 A | 7/1988 | Buettner-Janz et al. |
| 4,759,769 A | 7/1988 | Hedman et al. |
| 4,834,757 A | 5/1989 | Brantigan |
| 4,863,477 A | 9/1989 | Monson |
| 4,904,261 A | 2/1990 | Dove et al. |
| 4,917,704 A | 4/1990 | Frey et al. |
| 4,932,969 A | 6/1990 | Frey et al. |
| 4,946,378 A | 8/1990 | Hirayama et al. |
| 4,997,432 A | 3/1991 | Keller |
| 5,035,716 A | 7/1991 | Downey |
| 5,057,108 A | 10/1991 | Shetty et al. |
| 5,071,437 A | 12/1991 | Steffee |
| 5,108,438 A | 4/1992 | Stone |
| 5,122,130 A | 6/1992 | Keller |
| 5,195,526 A | 3/1993 | Michelson |
| 5,258,031 A | 11/1993 | Salib et al. |
| 5,282,861 A | 2/1994 | Kaplan |
| 5,306,308 A | 4/1994 | Gross et al. |
| 5,314,477 A | 5/1994 | Marnay |
| 5,320,644 A | 6/1994 | Baumgartner |
| 5,370,697 A | 12/1994 | Baumgartner |
| 5,394,457 A | 2/1995 | Leibinger et al. |
| 5,397,359 A * | 3/1995 | Mittelmeier ......... A61C 8/0012 623/1.5 |
| 5,401,269 A | 3/1995 | Buttner-Janz et al. |
| 5,415,704 A | 5/1995 | Davidson |
| 5,458,641 A * | 10/1995 | Ramirez Jimenez ..... A61F 2/44 403/43 |
| 5,458,642 A | 10/1995 | Beer et al. |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Büttner-Janz |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,709,683 A | 1/1998 | Bagby |
| 5,728,159 A | 3/1998 | Stroever et al. |
| 5,741,253 A | 4/1998 | Michelson |
| 5,776,198 A | 7/1998 | Rabbe et al. |
| 5,782,832 A | 7/1998 | Larsen et al. |
| 5,797,909 A | 8/1998 | Michelson |
| 5,824,094 A | 10/1998 | Serhan et al. |
| 5,836,846 A | 11/1998 | Hewko et al. |
| 5,865,846 A | 2/1999 | Bryan et al. |
| 5,865,848 A | 2/1999 | Baker |
| 5,888,226 A | 3/1999 | Rogozinski |
| 5,895,428 A | 4/1999 | Berry |
| 5,899,901 A | 5/1999 | Middleton |
| 5,899,911 A | 5/1999 | Carter |
| 5,928,284 A | 7/1999 | Mehdizadeh |
| 5,989,251 A | 11/1999 | Nichols |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,761 A | 3/2000 | Li et al. |
| 6,039,763 A | 3/2000 | Shelokov |
| 6,080,155 A | 6/2000 | Michelson |
| 6,083,228 A | 7/2000 | Michelson |
| 6,086,613 A | 7/2000 | Camino et al. |
| 6,096,038 A | 8/2000 | Michelson |
| 6,132,465 A | 10/2000 | Ray et al. |
| 6,136,031 A | 10/2000 | Middleton |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,174,311 B1 | 1/2001 | Branch et al. |
| 6,176,881 B1 | 1/2001 | Schaer et al. |
| 6,193,757 B1 | 2/2001 | Foley et al. |
| 6,224,595 B1 | 5/2001 | Michelson |
| 6,224,607 B1 | 5/2001 | Michelson |
| 6,224,630 B1 * | 5/2001 | Bao ................. A61L 31/048 623/16.11 |
| 6,231,609 B1 | 5/2001 | Mehdizadeh |
| 6,235,030 B1 | 5/2001 | Zucherman et al. |
| 6,245,109 B1 * | 6/2001 | Mendes ................ A61B 5/06 623/18.11 |
| 6,261,296 B1 | 7/2001 | Aebi et al. |
| 6,264,695 B1 | 7/2001 | Stoy |
| 6,290,726 B1 | 9/2001 | Pope et al. |
| 6,296,664 B1 | 10/2001 | Middleton |
| 6,315,797 B1 | 11/2001 | Middleton |
| 6,322,567 B1 | 11/2001 | Mittelstadt et al. |
| 6,336,941 B1 | 1/2002 | Subba Rao et al. |
| 6,348,071 B1 | 2/2002 | Steffee et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,395,032 B1 | 5/2002 | Gauchet |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,447,544 B1 | 9/2002 | Michelson |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Kuras |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer et al. |

(56) References Cited

U.S. PATENT DOCUMENTS

| | | |
|---|---|---|
| 6,666,866 B2 | 12/2003 | Martz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,686,437 B2 * | 2/2004 | Buchman ............... A61L 27/18 128/898 |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,719,794 B2 | 4/2004 | Gerber et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,752,832 B2 | 6/2004 | Neumann |
| 6,755,841 B2 | 6/2004 | Fraser et al. |
| 6,764,512 B2 | 7/2004 | Keller |
| 6,764,515 B2 | 7/2004 | Ralph et al. |
| 6,770,095 B2 | 8/2004 | Grinberg et al. |
| 6,790,233 B2 | 9/2004 | Brodke et al. |
| 6,793,678 B2 * | 9/2004 | Hawkins ............... A61F 2/4425 623/17.15 |
| 6,814,737 B2 | 11/2004 | Cauthen |
| 6,821,298 B1 | 11/2004 | Jackson |
| 6,827,740 B1 | 12/2004 | Michelson |
| 6,830,570 B1 | 12/2004 | Frey et al. |
| 6,846,328 B2 | 1/2005 | Cauthen |
| 6,852,126 B2 | 2/2005 | Ahlgren |
| 6,863,673 B2 | 3/2005 | Gerbec et al. |
| 6,875,213 B2 | 4/2005 | Michelson |
| 6,896,680 B2 | 5/2005 | Michelson |
| 6,899,735 B2 | 5/2005 | Coates et al. |
| 6,936,071 B1 | 8/2005 | Marnay et al. |
| 6,936,132 B2 | 8/2005 | Topolnitsky |
| 6,964,686 B2 | 11/2005 | Gordon |
| 6,966,929 B2 | 11/2005 | Mitchell |
| 6,966,931 B2 | 11/2005 | Huang |
| 6,986,788 B2 | 1/2006 | Paul et al. |
| 6,989,011 B2 | 1/2006 | Paul et al. |
| 6,994,727 B2 | 2/2006 | Khandkar et al. |
| 7,011,684 B2 | 3/2006 | Eckman |
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,156,876 B2 | 1/2007 | Moumene et al. |
| 7,169,182 B2 | 1/2007 | Errico et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,082 B2 | 6/2007 | Bartish et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,582 B2 | 12/2007 | Brady et al. |
| 7,303,583 B1 | 12/2007 | Schaer et al. |
| 7,318,839 B2 | 1/2008 | Malberg et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | De Villiers et al. |
| 7,452,380 B2 | 11/2008 | Zubok et al. |
| 7,491,241 B2 | 2/2009 | Errico et al. |
| 7,494,508 B2 | 2/2009 | Zeegers et al. |
| 7,517,363 B2 | 4/2009 | Rogers et al. |
| 7,531,001 B2 | 5/2009 | De Villiers et al. |
| 7,549,995 B2 | 6/2009 | Schultz |
| 7,563,284 B2 | 7/2009 | Coppes et al. |
| 7,563,286 B2 | 7/2009 | Gerber et al. |
| 7,575,599 B2 | 8/2009 | Villiers et al. |
| 7,585,326 B2 | 9/2009 | De Villiers et al. |
| 7,637,913 B2 | 12/2009 | De Villiers et al. |
| 7,708,776 B1 | 5/2010 | Blain et al. |
| 7,708,777 B2 | 5/2010 | O'Neil et al. |
| 7,731,753 B2 | 6/2010 | Reo et al. |
| 7,731,754 B2 | 6/2010 | De Villiers et al. |
| 7,753,956 B2 | 7/2010 | De Villiers et al. |
| 8,202,320 B2 | 6/2012 | Burgess et al. |
| 9,011,544 B2 | 4/2015 | Arramon et al. |
| 2001/0016773 A1 | 8/2001 | Serhan et al. |
| 2001/0029377 A1 | 10/2001 | Aebi et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0023306 A1 | 1/2003 | Liu et al. |
| 2003/0028249 A1 | 2/2003 | Baccelli et al. |
| 2003/0028250 A1 | 2/2003 | Reiley et al. |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree et al. |
| 2003/0083747 A1 | 5/2003 | Winterbottom et al. |
| 2003/0100951 A1 | 5/2003 | Serhan et al. |
| 2003/0125739 A1 | 7/2003 | Bagga et al. |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233155 A1 | 12/2003 | Slemmer et al. |
| 2004/0002761 A1 | 1/2004 | Rogers et al. |
| 2004/0024407 A1 | 2/2004 | Ralph et al. |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Ferree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0143270 A1 | 7/2004 | Zucherman et al. |
| 2004/0143332 A1 | 7/2004 | Krueger et al. |

(56) References Cited

U.S. PATENT DOCUMENTS

| | | |
|---|---|---|
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0243238 A1 | 12/2004 | Arnin et al. |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |
| 2005/0021145 A1 | 1/2005 | De Villiers et al. |
| 2005/0021146 A1 | 1/2005 | De Villiers et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg et al. |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0154467 A1 | 7/2005 | Peterman et al. |
| 2005/0165408 A1 | 7/2005 | Puno et al. |
| 2005/0171604 A1 | 8/2005 | Michalow |
| 2005/0192586 A1 | 9/2005 | Zucherman et al. |
| 2005/0192670 A1 | 9/2005 | Zubok et al. |
| 2005/0197706 A1 | 9/2005 | Hovorka et al. |
| 2005/0216081 A1 | 9/2005 | Taylor et al. |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0015183 A1 | 1/2006 | Gilbert et al. |
| 2006/0020342 A1 | 1/2006 | Ferree et al. |
| 2006/0025862 A1 | 2/2006 | Villiers et al. |
| 2006/0029186 A1 | 2/2006 | De Villiers et al. |
| 2006/0030857 A1 | 2/2006 | De Villiers et al. |
| 2006/0030862 A1 | 2/2006 | De Villiers et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0052870 A1 | 3/2006 | Ferree |
| 2006/0064169 A1 | 3/2006 | Ferree |
| 2006/0069439 A1 | 3/2006 | Zucherman et al. |
| 2006/0116768 A1 | 6/2006 | Krueger et al. |
| 2006/0142858 A1 | 6/2006 | Colleran et al. |
| 2006/0142862 A1 | 6/2006 | Diaz et al. |
| 2006/0155378 A1 | 7/2006 | Eckman |
| 2006/0167549 A1 | 7/2006 | Mathys, Jr. et al. |
| 2006/0178744 A1 | 8/2006 | De Villiers et al. |
| 2006/0178746 A1 | 8/2006 | Bartish, Jr. et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0241766 A1 | 10/2006 | Felton et al. |
| 2006/0259144 A1 | 11/2006 | Trieu |
| 2006/0259146 A1 | 11/2006 | Navarro et al. |
| 2006/0265068 A1 | 11/2006 | Schwab |
| 2006/0265077 A1 | 11/2006 | Zwirkoski |
| 2006/0293752 A1 | 12/2006 | Moumene et al. |
| 2006/0293753 A1 | 12/2006 | Thramann |
| 2006/0293754 A1 | 12/2006 | Devilliers et al. |
| 2007/0010826 A1 | 1/2007 | Rhoda et al. |
| 2007/0021837 A1 | 1/2007 | Ashman |
| 2007/0032875 A1 | 2/2007 | Blacklock et al. |
| 2007/0061011 A1 | 3/2007 | De Villiers et al. |
| 2007/0067035 A1 | 3/2007 | Falahee |
| 2007/0073398 A1 | 3/2007 | Fabian et al. |
| 2007/0093898 A1 | 4/2007 | Schwab et al. |
| 2007/0100453 A1 | 5/2007 | Parsons et al. |
| 2007/0100454 A1 | 5/2007 | Burgess et al. |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0162133 A1 | 7/2007 | Doubler et al. |
| 2007/0168033 A1 | 7/2007 | Kim et al. |
| 2007/0168034 A1 | 7/2007 | Kim et al. |
| 2007/0168036 A1 | 7/2007 | Ainsworth et al. |
| 2007/0179615 A1 | 8/2007 | Heinz et al. |
| 2007/0213821 A1 | 9/2007 | Kwak et al. |
| 2007/0233077 A1 | 10/2007 | Khalili |
| 2007/0233247 A1 | 10/2007 | Schwab |
| 2007/0233248 A1 | 10/2007 | Schwab et al. |
| 2007/0233251 A1 | 10/2007 | Abdou |
| 2007/0270970 A1 | 11/2007 | Trieu |
| 2007/0282449 A1 | 12/2007 | De Villiers et al. |
| 2007/0299521 A1 | 12/2007 | Glenn et al. |
| 2008/0015698 A1 | 1/2008 | Marino et al. |
| 2008/0015701 A1 | 1/2008 | Garcia et al. |
| 2008/0021557 A1 | 1/2008 | Trieu |
| 2008/0051900 A1 | 2/2008 | De Villiers et al. |
| 2008/0051901 A1 | 2/2008 | De Villiers et al. |
| 2008/0109081 A1 | 5/2008 | Bao et al. |
| 2008/0125864 A1 | 5/2008 | De Villiers et al. |
| 2008/0125865 A1 | 5/2008 | Abdelgany et al. |
| 2008/0133011 A1 | 6/2008 | De Villiers et al. |
| 2008/0154301 A1 | 6/2008 | De Villiers et al. |
| 2008/0154382 A1 | 6/2008 | De Villiers et al. |
| 2008/0161930 A1 | 7/2008 | Carls et al. |
| 2008/0215155 A1 | 9/2008 | De Villiers et al. |
| 2008/0221696 A1 | 9/2008 | De Villiers et al. |
| 2008/0228274 A1 | 9/2008 | De Villiers et al. |
| 2008/0228277 A1 | 9/2008 | De Villiers et al. |
| 2008/0234828 A1 | 9/2008 | Wagner et al. |
| 2008/0294259 A1 | 11/2008 | De Villiers et al. |
| 2009/0043391 A1 | 2/2009 | De Villiers et al. |
| 2009/0048674 A1 | 2/2009 | Zubok et al. |
| 2009/0048677 A1 | 2/2009 | McLeod et al. |
| 2009/0076614 A1 | 3/2009 | Arramon |
| 2009/0105833 A1 | 4/2009 | Hovda et al. |
| 2009/0105834 A1 | 4/2009 | Hovda et al. |
| 2009/0105835 A1 | 4/2009 | Hovda et al. |
| 2009/0192617 A1 | 7/2009 | Arramon et al. |
| 2009/0205188 A1 | 8/2009 | De Villiers et al. |
| 2009/0210060 A1 | 8/2009 | De Villiers et al. |
| 2009/0222101 A1 | 9/2009 | De Villiers et al. |
| 2009/0276051 A1 | 11/2009 | Arramon et al. |
| 2009/0326656 A1 | 12/2009 | De Villiers et al. |
| 2010/0004746 A1 | 1/2010 | Arramon |
| 2010/0016972 A1 | 1/2010 | Jansen et al. |
| 2010/0016973 A1 | 1/2010 | De Villiers et al. |
| 2010/0030335 A1 | 2/2010 | Arramon |
| 2010/0049040 A1 | 2/2010 | De Villiers et al. |
| 2010/0069976 A1 | 3/2010 | De Villiers et al. |
| 2010/0076558 A1 | 3/2010 | De Villiers et al. |
| 2010/0087868 A1 | 4/2010 | Barr et al. |
| 2010/0100141 A1 | 4/2010 | De Villiers et al. |
| 2010/0179419 A1 | 7/2010 | De Villiers et al. |
| 2010/0268344 A1 | 10/2010 | De Villiers et al. |
| 2010/0312347 A1 | 12/2010 | Arramon et al. |

FOREIGN PATENT DOCUMENTS

| | | |
|---|---|---|
| EP | 0333990 A2 | 9/1989 |
| EP | 0333990 A3 | 5/1990 |
| EP | 0560140 A1 | 9/1993 |
| EP | 0560141 A1 | 9/1993 |
| EP | 0591712 A1 | 4/1994 |
| EP | 0820740 A1 | 1/1998 |
| EP | 1142544 A1 | 10/2001 |

(56) References Cited

FOREIGN PATENT DOCUMENTS

| | | | |
|---|---|---|---|
| EP | 1153582 A2 | 11/2001 |
| EP | 1153582 A3 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1405615 A1 | 4/2004 |
| EP | 1417940 A1 | 5/2004 |
| EP | 1570813 A1 | 9/2005 |
| EP | 1972309 A1 | 9/2008 |
| FR | 2803741 A1 | 7/2001 |
| JP | S61122859 A | 6/1986 |
| JP | S63164948 A | 7/1988 |
| JP | H01136655 A | 5/1989 |
| JP | H067391 A | 1/1994 |
| JP | 2002521090 A | 7/2002 |
| JP | 2003508119 A | 3/2003 |
| WO | WO-9920209 A1 | 4/1999 |
| WO | WO-9930651 A1 | 6/1999 |
| WO | WO-0004851 A1 | 2/2000 |
| WO | WO-0035384 A1 | 6/2000 |
| WO | WO-0042954 A2 | 7/2000 |
| WO | WO-0042954 A3 | 11/2000 |
| WO | WO-0101893 A1 | 1/2001 |
| WO | WO-0115637 A1 | 3/2001 |
| WO | WO-0168003 A1 | 9/2001 |
| WO | WO-0211650 A2 | 2/2002 |
| WO | WO-0211650 A3 | 9/2003 |
| WO | WO-2004000170 A1 | 12/2003 |
| WO | WO-2004000171 A1 | 12/2003 |
| WO | WO-2004026187 A1 | 4/2004 |
| WO | WO-2004054477 A1 | 7/2004 |
| WO | WO-2005004756 A2 | 1/2005 |
| WO | WO-2005004756 A3 | 5/2005 |
| WO | WO-2005053580 A1 | 6/2005 |
| WO | WO-2005072662 A1 | 8/2005 |
| WO | WO-2005112834 A2 | 12/2005 |
| WO | WO-2005112834 A3 | 5/2006 |
| WO | WO-2006119092 A2 | 11/2006 |
| WO | WO-2006119092 A3 | 12/2006 |
| WO | WO-2006128509 A1 | 12/2006 |
| WO | WO-2007121320 A2 | 10/2007 |
| WO | WO-2007121320 A3 | 6/2008 |
| ZA | 20039312 | 11/2003 |

OTHER PUBLICATIONS

Hellier, et al., Wear Studies for Development of an Intervertebral Disc Prosthesis. Spine, vol. 17 No. 6 Supplement pp. 86-96 (1992).
International search report and written opinion dated Sep. 18, 2009 for PCT/US2009/042892.
Lee, et al. Impact Response of the Intervertebral Disc in a Finite-Element Model. Spine. 2000; 25(19):2431-2439.
Lehuec, et al. Shock Absorption in Lumber Disc Prosthesis. Journal of Spinal Disorders & Techniques. 2003; 16(4):346-351.
Notice of allowance dated Mar. 26, 2015 for U.S. Appl. No. 12/857,806.
Notice of allowance dated Dec. 19, 2014 for U.S. Appl. No. 12/857,806.
Office action dated Feb. 14, 2012 for U.S. Appl. No. 12/857,806.
Office action dated Mar. 6, 2014 for U.S. Appl. No. 12/857,806.
Office action dated Mar. 11, 2014 for U.S. Appl. No. 12/435,572.
Office action dated Mar. 13, 2012 for U.S. Appl. No. 12/435,572.
Office action dated May 30, 2014 for U.S. Appl. No. 12/857,806.
Office action dated Jul. 20, 2012 for U.S. Appl. No. 12/857,806.
Office action dated Oct. 15, 2013 for U.S. Appl. No. 12/435,572.
Office action dated Oct. 26, 2011 for U.S. Appl. No. 12/435,572.
Office action dated Dec. 15, 2014 for U.S. Appl. No. 12/435,572.

\* cited by examiner

POLYARYLETHERKETONE ARTIFICIAL INTERVERTEBRAL DISC

CROSS-REFERENCES TO RELATED APPLICATIONS

This application is a continuation of U.S. patent application Ser. No. 12/435,572, filed May 5, 2009, which claims priority to U.S. Provisional Application No. 61/050,455, filed May 5, 2008, entitled "POLYARYLETHERKETONE ARTIFICIAL INTERVERTEBRAL DISC," and U.S. Provisional Application No. 61/082,012 filed Jul. 18, 2008, entitled "POLYARYLETHERKETONE ARTIFICIAL INTERVERTEBRAL DISC;" the full disclosures of which are incorporated herein by reference.

BACKGROUND OF THE INVENTION

The present invention relates to medical devices and methods. More specifically, the present invention relates to intervertebral disc prostheses.

Back pain takes an enormous toll on the health and productivity of people around the world. According to the American Academy of Orthopedic Surgeons, approximately 80 percent of Americans will experience back pain at some time in their life. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral discs cause a patient pain and discomfort, surgery is often required. Traditionally, surgical procedures for treating intervertebral discs have involved discectomy (partial or total removal of a disc), with or without fusion of the two vertebrae adjacent to the disc. Fusion of the two vertebrae is achieved by inserting bone graft material between the two vertebrae such that the two vertebrae and the graft material grow together. Oftentimes, pins, rods, screws, cages and/or the like are inserted between the vertebrae to act as support structures to hold the vertebrae and graft material in place while they permanently fuse together. Although fusion often treats the back pain, it reduces the patient's ability to move, because the back cannot bend or twist at the fused area. In addition, fusion increases stresses at adjacent levels of the spine, potentially accelerating degeneration of these discs.

In an attempt to treat disc related pain without fusion, an alternative approach has been developed, in which a movable, implantable, artificial intervertebral disc (or "disc prosthesis") is inserted between two vertebrae. A number of different artificial intervertebral discs are currently being developed. For example, U.S. Patent Publication Nos. 2005/0021146, 2005/0021145, and 2006/0025862, which are hereby incorporated by reference in their entirety, describe artificial intervertebral discs. This type of intervertebral disc has upper and lower plates positioned against the vertebrae and a mobile core positioned between the two plates to allow articulating, lateral and rotational motion between the vertebrae.

Another example of an intervertebral disc prostheses having a movable core is the CHARITE artificial disc (provided by DePuy Spine, Inc.) and described in U.S. Pat. No. 5,401,269. Other examples of intervertebral disc prostheses include MOBIDISK™ disc prosthesis (provided by LDR Medical), the BRYAN™ cervical disc prosthesis (provided by Medtronic Sofamor Danek, Inc.), and the PRODISC™ disc prosthesis (from Synthes Stratec, Inc.) and described in U.S. Pat. No. 6,936,071. Some of these intervertebral discs are mobile core discs while others have a ball and socket type two piece design. Although existing disc prostheses provide advantages over traditional treatment methods, improvements are ongoing.

The known artificial intervertebral discs generally include upper and lower plates which locate against and engage the adjacent vertebral bodies, and a core for providing motion between the plates. The core may be movable or fixed, metallic, ceramic or polymer and generally has at least one convex outer surface which mates with a concave recess on one of the plates in a fixed core device or both of the plates for a movable core device.

The known disc materials each have advantages and disadvantages. For example, ceramic and polymer materials generally cause less artifacts in medical imaging, such as an X-ray, CT or MRI image than metals. Metals may have better bone attachment properties than polymers and better wear characteristics than polymers and ceramics. However, on MRI metals can create artifacts that may obscure adjacent tissue and make visualization at the site of the artificial disc nearly impossible. The continuing challenge in forming artificial discs is to find the right combination of materials and design to use the benefits of the best materials available.

Therefore, a need exists for an improved artificial intervertebral disc with improved visibility in medical imaging, such as X-ray, MRI and CT imaging, and with an improved surface for bone ongrowth.

BRIEF SUMMARY OF THE INVENTION

According to the invention there is provided an intervertebral prosthesis for insertion between adjacent vertebrae, in one embodiment, the prosthesis comprising upper and lower prosthesis plates and a movable core. The prosthesis plates and optionally the core are formed of polyaryletherketone (PAEK) for improved imaging properties. A metallic insert is provided on each of the PAEK prosthesis plates providing a bone ongrowth surface.

According to another aspect of the invention an intervertebral prosthesis includes upper and lower prosthesis plates of PAEK configured to articulate with respect to one another by sliding motion of at least two bearing surfaces of the plates.

In accordance with one aspect of the present invention, an intervertebral disc includes an upper plate having an upper vertebra contacting surface and a lower bearing surface, wherein the upper plate is formed of polyaryletherketone (PAEK) with the upper surface formed at least in part from a metallic insert having a plurality of projections formed thereon for improving bone attachment; a lower plate having a lower vertebra contacting surface and an upper bearing surface, wherein the lower plate is formed of PAEK with the lower surface formed at least in part from a metallic insert having a plurality of projections formed thereon for improving bone attachment; and a core positioned between the upper and lower plates. The core has upper and lower surfaces configured to mate with the bearing surfaces of the upper and lower plates.

In accordance with another aspect of the invention, an intervertebral disc includes an upper plate, a lower plate, and a core positioned between the upper and lower plates. The upper plate has an upper vertebra contacting surface and a lower bearing surface and the upper plate is formed of polyaryletherketone (PAEK) with the upper surface formed at least in part from a metallic insert having a thickness of at least 0.3 mm. The lower plate has a lower vertebra contacting surface and an upper bearing surface and the lower plate is formed of PAEK with the lower surface formed at least in part from a metallic insert having a thickness of at least 0.3 mm. The core has upper and lower surfaces configured to mate with the bearing surfaces of the upper and lower plates.

In accordance with a further aspect of the invention an intervertebral disc includes an upper plate having an upper vertebra contacting surface and a lower bearing surface and a lower plate having a lower vertebra contacting surface and an upper bearing surface, wherein the upper and lower bearing surfaces are configured to allow articulation between the upper vertebra contacting surface and the lower vertebra contacting surface. The upper and lower plates are formed of polyaryletherketone (PAEK) with the vertebra contacting surfaces formed at least in part from a metallic insert having a plurality of projections formed thereon for improving bone attachment.

In accordance with an additional aspect of the invention an intervertebral disc includes an upper plate formed of polyaryletherketone (PAEK) with a metallic insert fixed to the PAEK and configured to contact a first vertebra and a lower plate formed of PAEK with a metallic insert fixed to the PAEK and configured to contact a second vertebra adjacent to the first vertebra. The upper and lower plates are arranged to articulate in a anterior-posterior direction and in a lateral direction with respect to one another and to rotate with respect to one another.

Other features of the invention are set forth in the appended claims.

DETAILED DESCRIPTION OF THE INVENTION

Figure 1:
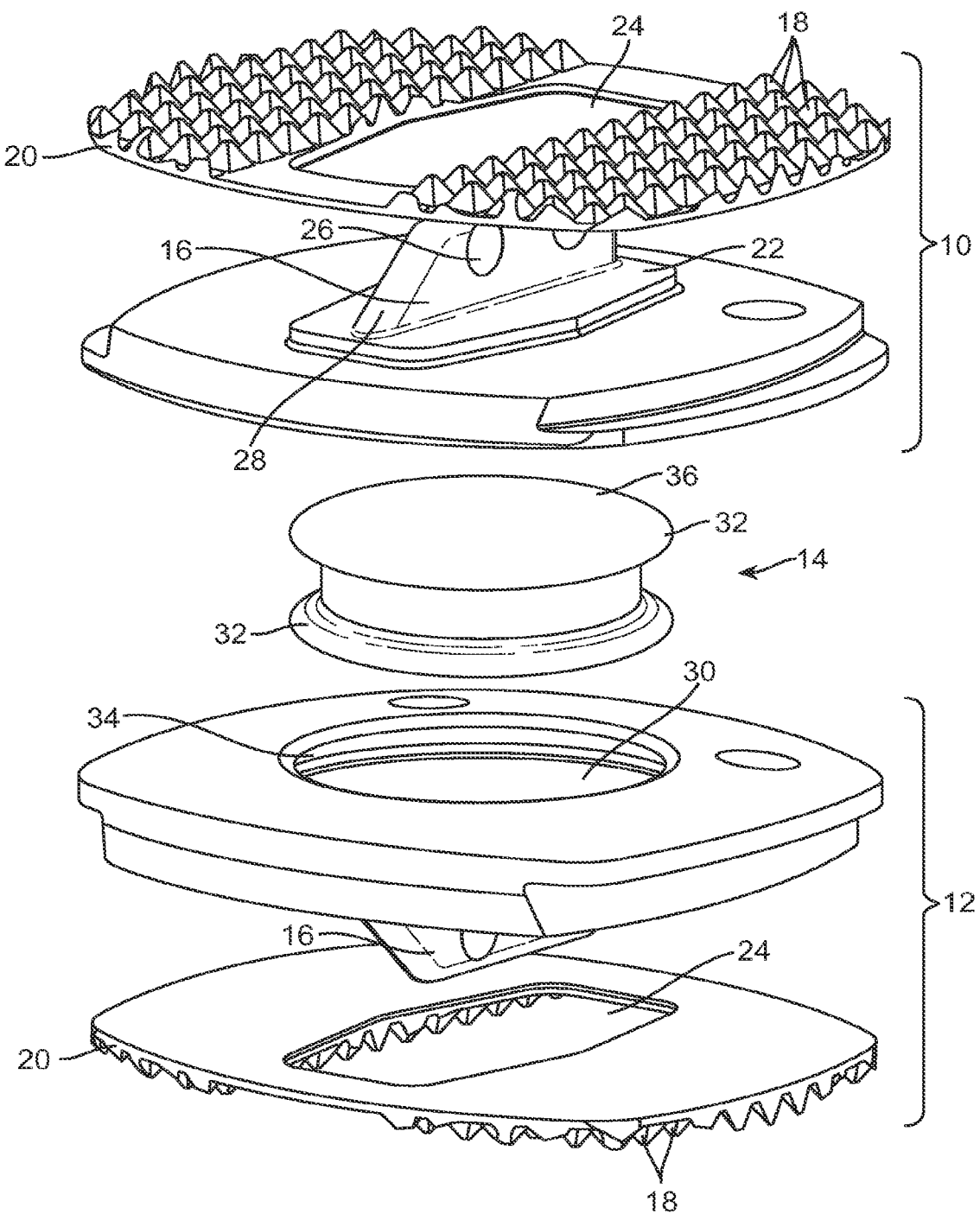
FIG. 1 is an exploded perspective view of an intervertebral disc according to one embodiment of the present invention.

FIG. 1 illustrates an intervertebral disc having an upper plate 10, a lower plate 12, and a core 14. The upper and lower plates 10, 12 are formed of a durable and imaging friendly material such a polyaryletherketone (PAEK), one example of which is neat poly(aryl-ether-ether-ketone) (PEEK). The PEEK portion of the upper and lower plates includes an inner bearing surface for contacting the core 14 and one or more fins 16. The upper and lower plates 10, 12 also include one or more metallic inserts 20 formed of a material which serves as a bone integration surface. The inserts 20 may include one or more bone integration enhancing features such a serrations or teeth to ensure bone integration. As shown in the embodiment of FIG. 1, the bone integration enhancing features include serrations 18. The metallic inserts 20 may be formed in a variety of shapes and with a variety of bone integration features, however, the metallic inserts cover a substantial portion of the bone contacting surfaces of the plates 10, 12.

The metallic inserts 20 shown in FIG. 1 are in the form of screens formed of titanium or other metal by stamping, machining or the like. The screens 20 can be securely or loosely fixed to the outer surfaces of the plates 10, 12. Titanium screens 20 form surfaces which provide both immediate fixation by way of the serrations 18 and optional teeth and provides a bone ongrowth surface for long term stability. In addition to providing fixation, the inserts or screens 20 also can serve as a radiographic marker. Since PEEK is radiolucent or nearly invisible under medical imaging, the inserts 20 serve as markers to identify the limits of the disc and evaluate the performance of the disc under X-ray, fluoroscopy, MRI or CT scan.

PEEK is part of the family of polyaryletherketones (PAEKs), also called polyketones, which have been increasingly employed as implantable materials for orthopedic implants. PAEK is a family of inherently strong and biocompatible high temperature thermoplastic polymers, consisting of an aromatic backbone molecular chain, interconnected by ketone and ether functional groups. The PAEK family includes poly(aryl-ether-ether-ketone) (PEEK), poly(aryl-ether-ketone-ether-ketone-ketone) (PEKEKK), and poly(ether-ketone-ketone) (PEKK) and was originally developed in the aircraft industry for its stability at high temperatures and high strength.

The upper and lower plates 10, 12 can be fabricated from a number of different PAEK materials including neat (unfilled) PEEK, PEEK-OPTIMA available from Invibio, Inc., fiber reinforced PEEK, such as PEEK-CFR (carbon fiber reinforced) from Invibio, Inc., glass fiber reinforced PEEK, ceramic filled PEEK, Teflon filled PEEK, barium sulfate filled PEEK or other reinforced or filled PAEK materials. These PAEK materials are stable, bio-inert, and strong making them ideally suited for the base material for an articulating joint. However, other materials which are invisible or near invisible under radiographic imaging, are bio-inert and have high strength can also be used. Although neat PEEK has an elastic modulus of 3-4 GPa, fiber reinforcing the PEEK can bring the modulus up to match cortical bone (18 GPa) or to match titanium (105-120 GPa).

As shown in FIG. 1, the fin 16 is surrounded by a raised portion or rim 22 which is received within an opening 24 in the screen 20. The rim 22 and surrounding opening 24 serve to locate the screen on the surface of the plate 10. The rim 22 and opening 24 can provide a snap lock feature for holding the screen 20 in place. Alternate fixation means for the screen 20 include insert molding, peripheral locking features, or adhesives. In one embodiment, the screen 20 and the PEEK plate are not fixed together. In the unfixed embodiment, the rim 22 and opening 24 prevent sliding movement of the screen over the surface of the plate while the screen is prevented from lifting off of the PEEK by the natural anatomy once the disc has been implanted.

The screen 20 is preferably a thin screen having a thickness of about 0.1 mm to about 1.0 mm preferably about 0.3-0.7 mm not including a height of any serrations or teeth. The screen 20 preferably covers a significant portion of the bone contacting surface of the disc, such as at least 50% of the bone contacting surface (not including any fins) and preferably at least 75% of the bone contacting surface.

In one embodiment, the screen 20 ends before the posterior edge of the plate 10 to allow improved imaging of the spinal column by moving the metallic portion of the disc further from the posterior edge of the plate. In another embodiment, the bone contacting surface is partially, i.e. 50%, covered by the screen 20 and a remainder of the bone contacting surface and optionally the fin is covered with a titanium plasma spray coating for improved bone ongrowth. Since the plasma spray coating can be formed thinner than the screen 20, the imaging can be further enhanced by the reduced metal provided by a combination of a screen and coating.

The fin 16 can be an elongate fin pierced by one or more transverse holes 26. The disc can be inserted posteriorly into the patient from an anterior access, such that an angled posterior end 28 of fin 16 can enter a groove in one of the vertebrae as a posterior side of the intervertebral disc enters the intervertebral space followed by an anterior side of the intervertebral disc.

On opposite surfaces of the plates 10, 12 from the titanium screens 20 the plates are formed with recesses 30 which serve as bearing surfaces for the core 14. Although the bearing surfaces are shown as PEEK bearing surfaces, metal bearing surface inserts, such as cobalt chromium alloy bearing surface inserts may also be used.

The core 14 can be formed as a circular disc shaped member with upper and lower bearing surfaces 36 which match the curvature of the recesses or bearing surfaces 30 of the plates 10, 12. The core 14 also has one or more annular rims 32 which cooperate with a retention feature 34 on at least one of the discs to retain the core between the plates when the intervertebral disc is implanted between the vertebrae of a patient. The core 14 is moveable with respect to both the upper and lower discs to allow articulation, translation and rotation of the upper and lower plates with respect to one another. The spherically curved outer surfaces 36 of the core 14 and bearing surfaces 30 of the plates 10, 12 have the same radius of curvature which may vary depending on the size of the intervertebral disc.

Although the bearing surfaces have been shown as spherically curved surfaces, other shaped surfaces may also be used. For example, one flat bearing surface and one spherical surface may be used. Alternatively, asymmetrical bearing surfaces on the plates and the core may be used to limit rotational motion of the disc, such as oval or kidney bean shaped bearing surfaces.

In one embodiment of the invention, the core 14 has a radius of curvature which is slightly smaller than a radius of curvature of the corresponding bearing surface 30 of the plate 10, 12. The slight difference in radius of curvature is on the order of a 0.5 to 5 percent reduction in radius of curvature for the core. The slight difference in curvature can improve articulation by reducing any possible initial sticking of the bearing surfaces, and is particularly useful for a combination of a PEEK core and PEEK bearing surfaces.

In the embodiment shown in FIG. 1 a single central fin 16 is provided on each of the plates 10, 12 extending in an anterior posterior direction with an angled posterior edge for aiding in insertion. This embodiment is particularly useful for insertion from an anterior side of the intervertebral disc space. Alternatively, two or more fins 16 can also be provided on each plate. In one example, a single fin can be provided on one plate while a double fin can be provided on the other plate to achieve a staggered arrangement particularly useful for multi-level disc implant procedures. This staggered arrangement prevents the rare occurrence of vertebral body splitting by avoiding cuts to the vertebral body in the same plane for multi-level implants. The orientation of the fin(s) 16 can also be modified depending on the insertion direction for the intervertebral disc 10. In alternative embodiments, the fins 16 may be rotated away from the anterior-posterior axis, such as in a lateral-lateral orientation, a posterolateral-anterolateral orientation, or the like.

In one two fin embodiment of a plate, the two fins are formed from the metal as a part of the screen. In this embodiment, two fin shaped members are cut into the flat screen and folded upwards to form the two fins. This leaves a gap between the fins that may be left as PEEK surface or may be plasma spray coated with titanium.

The fins 16 are configured to be placed in slots cut in the vertebral bodies. In one embodiment, the fins 16 are pierced by transverse holes 26 for bone ongrowth. The transverse holes 26 may be formed in any shape and may extend partially or all the way through the fins 16. Preferably, the fins 16 each have a height greater than a width and have a length greater than the height.

The fins 16 provide improved attachment to the bone and prevent rotation of the plates in the bone. In some embodiments, the fins 16 may extend from the surface of the plates 10, 12 at an angle other than 90.degree. For example on one or more of the plates 10, 12 where multiple fins 16 are attached to the surface the fins may be canted away from one another with the bases slightly closer together than their edges at an angle such as about 80-88 degrees. The fins 16 may have any other suitable configuration including various numbers angles and curvatures, in various embodiments. In some embodiments, the fins 16 may be omitted altogether.

In addition to the fins 16, the bone integration may be improved by providing the metallic inserts or screens 20 with a plurality of projections formed thereon for improving bone attachment. In FIG. 1, the projections are in the form of pyramid shaped serrations 18 arranged in a plurality of rows on either side of the opening 24.

The projections may also include one or more finlets, teeth, or the like. The projections can be positioned in varying numbers and arrangements depending on the size and shape of the plate used. In one example 4-6 wedge shaped teeth are provided on each metallic insert 20 for cervical applications. Other teeth shapes may also be used, for example pyramidal, conical, rectangular and/or cylindrical teeth. The teeth and/or finlets can have varying heights which can be about 0.7-3 mm, preferably about 1-2 mm. The serrations can have heights varying from about 0.3-1 mm. With passage of time, firm connection between the screens 20 and the vertebrae will be achieved as bone tissue grows over the serrated finish, teeth and/or finlets. Bone tissue growth will also take place about the fins 16 and through the holes 26 therein, further enhancing the connection which is achieved.

Other geometries of bone integration structures may also be used including teeth, grooves, ridges, pins, barbs or the like. When the bone integration structures are ridges, teeth, barbs or similar structures, they may be angled to ease insertion and prevent migration. These bone integration structures can be used to precisely cut the bone during implantation to cause bleeding bone and encourage bone integration. Additionally, the outer surfaces of the plates 10, 12 may be provided with a rough microfinish formed by blasting with aluminum oxide microparticles or the like to improve bone integration. In some embodiments, the outer surface may also be titanium plasma sprayed or HA coated to further enhance attachment of the outer surface to vertebral bone.

Figure 2:
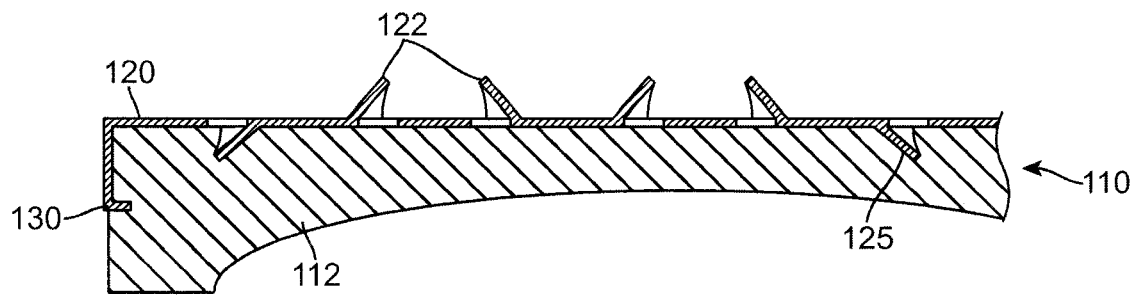
FIG. 2 is a side cross sectional view of a portion of an upper plate for an intervertebral disc according to another embodiment of the present invention.
Figure 3:
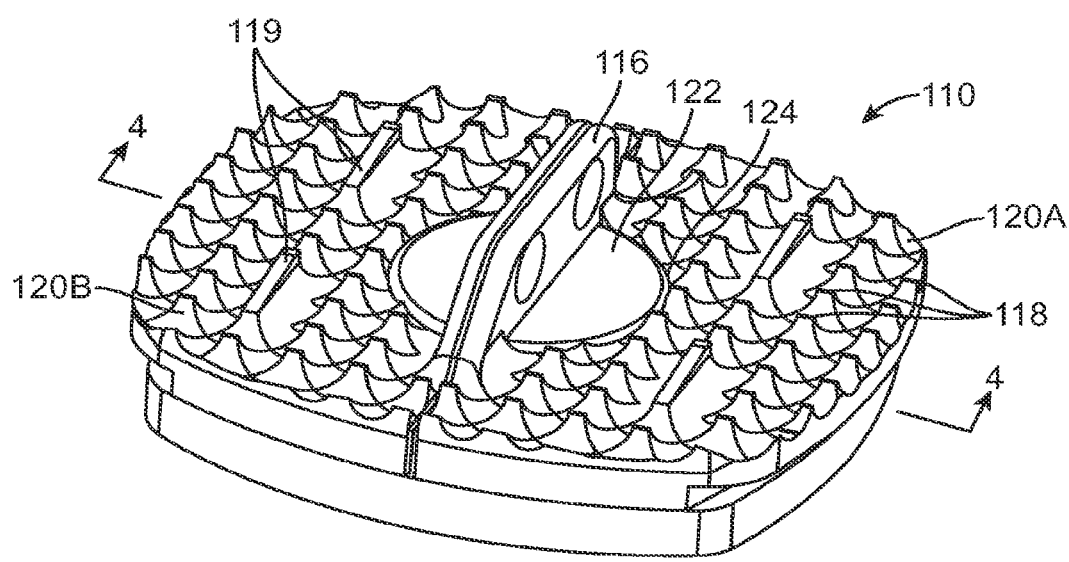
FIG. 3 is a perspective view of a plate for an intervertebral disc according to an alternative embodiment of the present invention.

The screens 20 are shown in FIG. 1 as machined flat plates with a plurality of protrusions. As shown in FIG. 2, the screens may also take the form of a thin metal plate which has been stamped with a pattern of holes forming bone engaging teeth in a vertebra contacting direction and/or a pattern of holes forming securing teeth for securing the screen to the PEEK plates. FIG. 2 shows an upper plate 110 of an alternative intervertebral disc. The upper plate includes a PEEK portion 112 and a metallic screen 120 on the vertebral body contacting surface of the PEEK portion. The metallic screen 120 includes a plurality of punched teeth 122 arranged to function in the manner of the serrations 18 of FIG. 1 to provide improved fixation. The metallic screen 120 can also include a plurality of teeth 125 arranged to secure the screen to the PEEK portion 112. In one example, the PEEK portion 112 can be insert molded around the teeth 125.

FIG. 2 also illustrates a locking feature 130 for locking the screen portion 120 to the PEEK or polymer portion 112. The locking feature 130 may include a snap lock feature, an insert molded feature, or other mechanical connection. The locking feature 130 may be provided on two or more sides of the upper plate 110 and may be discrete or continuous. The same or a different locking feature may be used on the corresponding lower plate. The above described features of FIG. 2 can be combined with many of the structures shown in FIG. 1.

The core 14 according to the embodiment of FIG. 1 can be retained in the lower plate 12 by retention feature 34 comprising a retention ring that protrudes inwardly from an edge of the lower plate 12. Although a circumferential core retaining feature is shown, other core retaining features may also be used including at least those shown in U.S. Patent Publication Nos. 2005/0251262, 2005/0021146, and 2005/0021145, which are incorporated herein by reference in their entirety.

Although the core 14 has been shown as circular in cross section with spherically shaped bearing surfaces 36, other shapes may be used including oval, elliptical, or kidney bean shaped. These non-circular shaped cores can be used to limit rotational motion between the upper and lower plates 10, 12. Although the core 14 and plates 10, 12 have been shown as solid members, the core and plates may be made in multiple parts and/or of multiple materials. The core can be made of low friction materials, such as titanium, titanium nitrides, other titanium based alloys, tantalum, nickel titanium alloys, stainless steel, cobalt chrome alloys, ceramics, or biologically compatible polymer materials including PEEK, UHMWPE, PLA or fiber reinforced polymers. High friction coating materials can also be used.

When the core 14 is formed of a polymer such as PEEK which is invisible under radiographic imaging, it may be desirable to have a radiographic marker imbedded within the core. For example, a single titanium pin may be positioned axially through a center of the core so that the PEEK core is visible in a post-operative X-ray examination. Other arrangements of pins, such as one or more radial pins, can also serve as radiographic markers and enable the position of the core 14 to be ascertained during such examination.

Alternatively, a PEEK core may be made more visible on radiographic examination by selection of the particular PEEK material or reinforcing material in the event of a reinforced PEEK material. In one embodiment, the PEEK core 14 is formed of a PEEK material with a different density (greater visibility) than that of the plates 10, 12 to allow the core to be distinguished from the plates in X-ray. One PEEK material which may be used to form a visible core is PEEK loaded with barium sulfate. The barium sulfate loaded PEEK may also be used to improve lubricity of the core and improve sliding of the bearing surfaces over the core.

As an alternative to a PEEK core, a metallic core may be used. The metallic core, if of relatively small size, can be used with minimal distortion of an MRI or CT scan image because the core is positioned away from an area of interest for imaging, while the PEEK plates are located closest to the area of interest. A metal coated PEEK core can provide the combined benefits of the two materials. The metallic core provides the combined benefits of improved lubricity and decrease wear from metal on PEEK bearing surfaces. Alternately, the PEEK plates may be formed with a metallic bearing surface by providing a thin cup shaped bearing surface insert on the PEEK plates. The bearing surface inserts can be on the order of 1 mm or less in thickness and formed of titanium or cobalt chromium alloy. The PEEK plates with metallic bearing surface inserts can minimizes the amount of metal for improved imaging and be used in combination with a PEEK core.

The intervertebral disc according to the present invention provides articulation in two directions as well as rotation. The degree of articulation and rotation can be limited depending on the application or for a particular patient.

The plates 10, 12 are provided with grooves 34A at their lateral edges for use in grasping the disc by an instrument to facilitate holding and manipulation of the disc for insertion or removal of the disc. The grooves 34A allow the plates 10, 12 to be grasped and inserted simultaneously in a locked orientation. Other alternate grasping configurations including annular grooves or blind bores can also be used.

The upper and lower plates 10, 12 are preferably formed from PEEK or other high strength biocompatible polymer. Portions of the upper and lower plates 10, 12, such as the screens 20 may also be formed from titanium, titanium nitrides, other titanium based alloys, tantalum, nickel titanium alloys, stainless steel, cobalt chrome alloys, ceramics, or biologically compatible polymer materials including UHMWPE, PLA or fiber reinforced polymers. The bearing surfaces 30 can have a hard coating such as a titanium nitride finish.

Portions of the plates 10, 12 may be treated with a titanium plasma spray to improve bone integration. For example, the surfaces of the fins 16 may be titanium plasma spray coated. In another example, the fin 16 and screen 20 may be titanium plasma sprayed together. Other materials and coatings can also be used such as HA (hydroxylapatite) coating, micro HA coating, blasting procedures for surface roughing, and/or other bone integration promoting coatings. Any suitable technique may be used to couple materials together, such as snap fitting, slip fitting, lamination, interference fitting, use of adhesives, welding and/or the like.

The intervertebral disc described herein is surgically implanted between adjacent spinal vertebrae in place of a damaged disc. Those skilled in the art will understand the procedure of preparing the disc space and implanting the disc which is summarized herein. In a typical artificial disc procedure, the damaged disc is partially or totally removed and the adjacent vertebrae are forcibly separated from one another or distracted to provide the necessary space for insertion of the disc. One or more slots are cut into the vertebrae to accommodate the fins 16 if any. The plates 10, 12 are slipped into place between the vertebrae with their fins 16 entering slots cut in the opposing vertebral surfaces to receive them. The plates may be inserted simultaneously or sequentially and with or without the core. After partial insertion of the disc, the individual plates 10, 12 can be further advanced independently or together to a final position. Once the disc has been inserted, the vertebra move together to hold the assembled disc in place.

The vertebral contacting surfaces of the plates 10, 12 including the serrations 18 and the fins 16 locate against the opposing vertebrae and, with passage of time, firm connection between the plates and the vertebrae will be achieved as bone tissue grows over the serrated finish and through and around the fin.

The disc and surrounding anatomy can be visualized post operatively by X-ray, fluoroscopy, CT scan, MRI, or other medical imaging techniques. In the event of excessive wear of the bearing surfaces of the core 14, the core can be removed and replaced in an additional surgical procedure.

Figure 7:
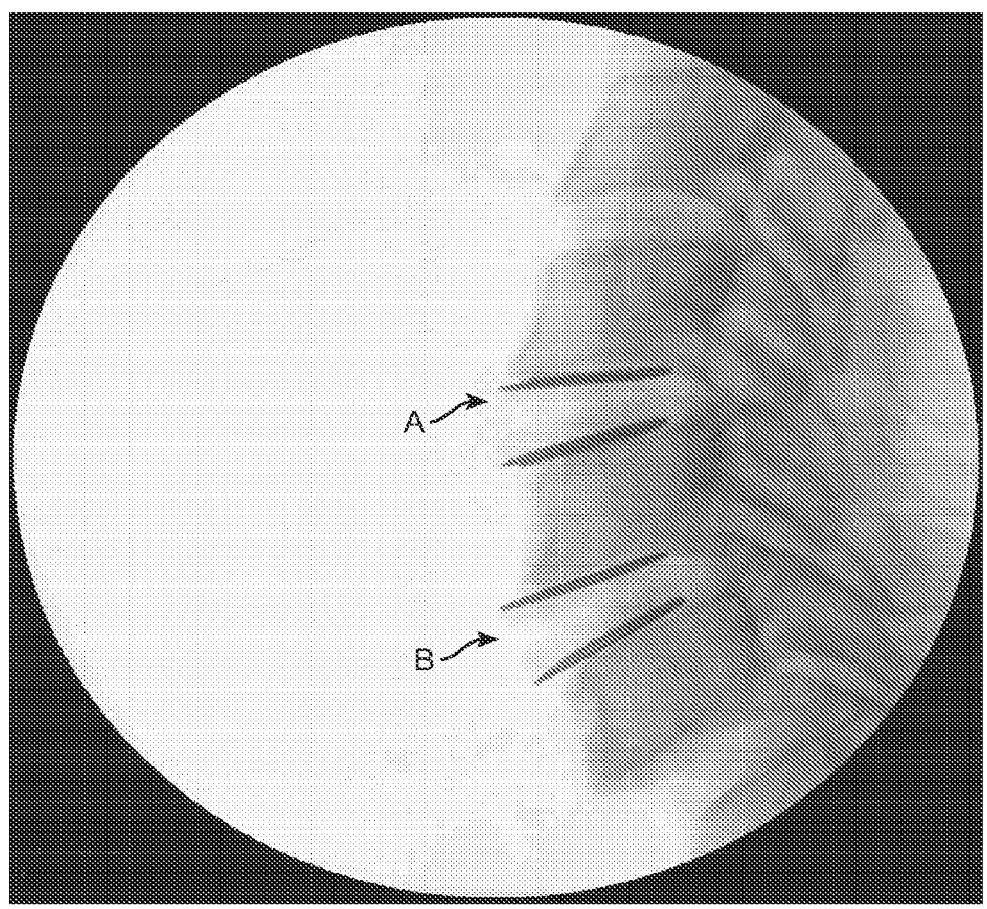
FIG. 7 is an X-ray image of two intervertebral discs according to the embodiment of FIG. 1 implanted in a spine.
Figure 8:
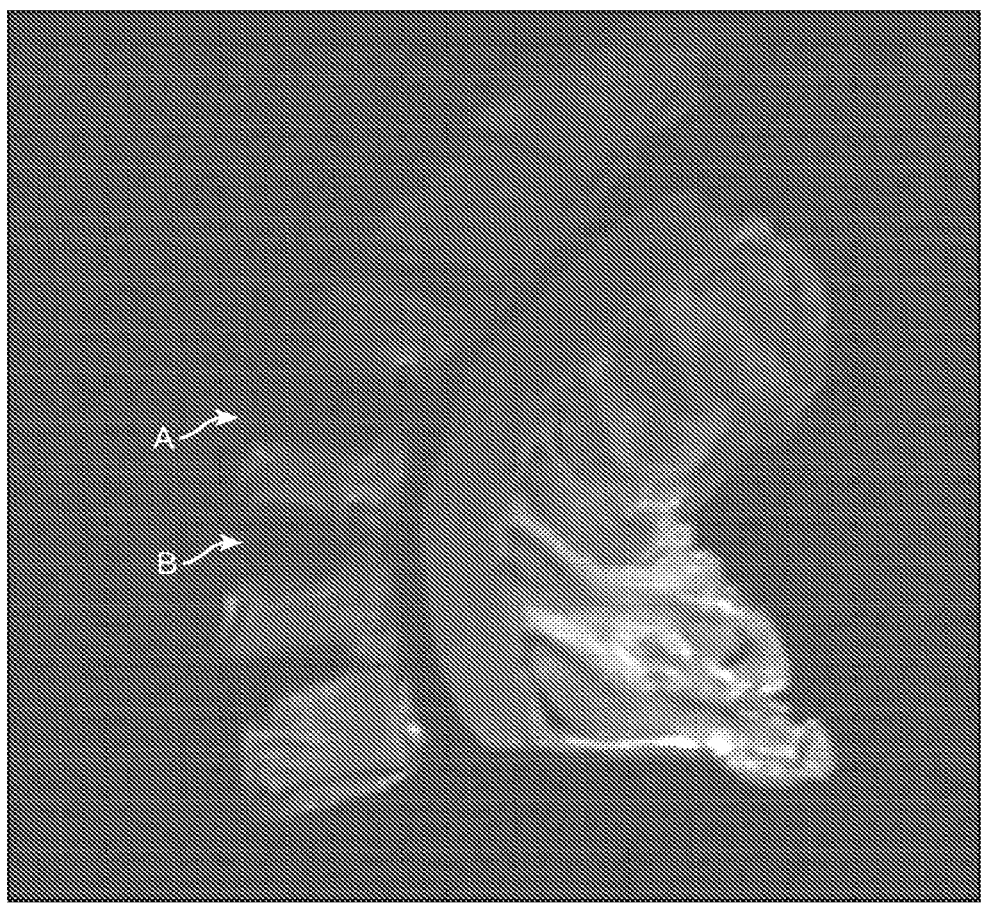
FIG. 8 is an MRI image of the two intervertebral discs shown in the X-ray of FIG. 7.
Figure 9:
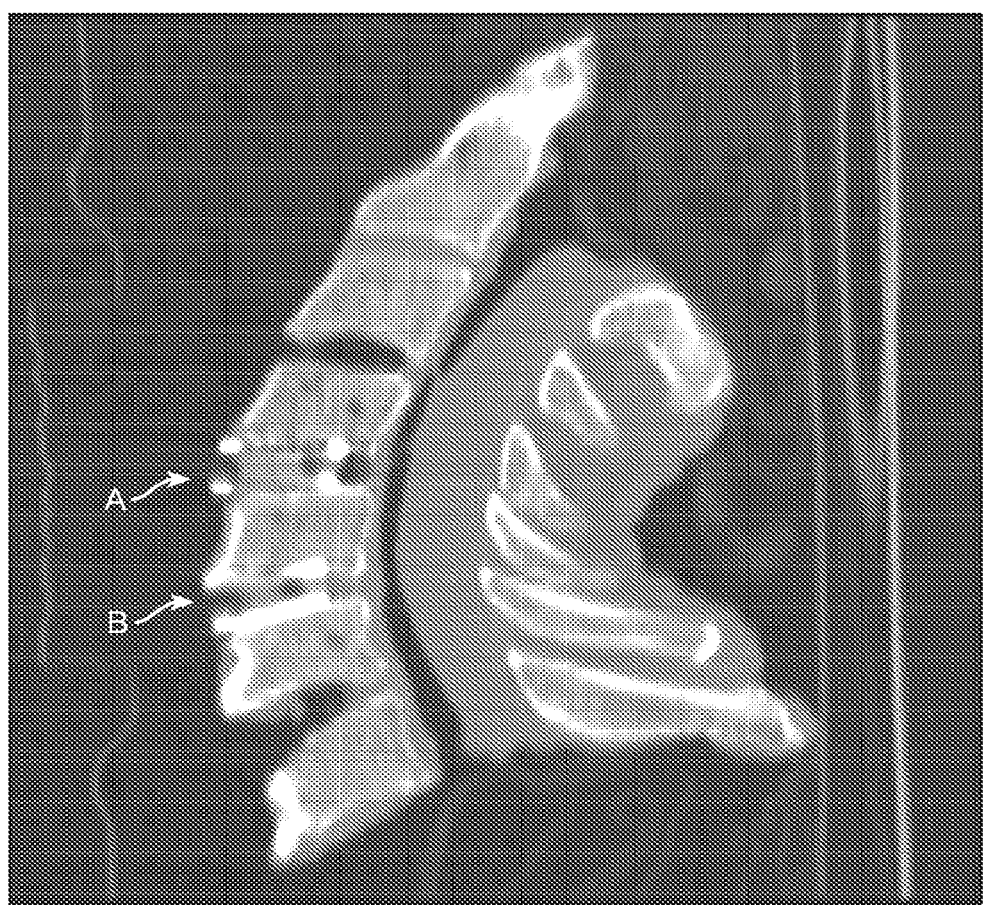
FIG. 9 is a CT scan image of the two intervertebral discs shown in the X-ray of FIG. 7.

FIGS. 7, 8 and 9 are images showing two of the intervertebral discs of FIG. 1 implanted in a spine at two adjacent cervical disc levels. The images are taken by X-ray (FIG. 7), MRI (FIG. 8) and CT scan (FIG. 9). The intervertebral disc shown at A in the images has serrations 18 on the screens 20 as shown in FIG. 1. The intervertebral disc shown at B in the images has no serrations. Both of the discs are formed with neat PEEK plates and cores and titanium screens. As can be seen in the X-ray image, the titanium screens 20 are clearly visible, while the PEEK portion of the plates 10, 12 and the PEEK core are completely invisible under X-ray. With some adjustment of the contrast of the X-ray image, the PEEK portion of the plates can be visualized slightly. The MRI and CT images clearly show the vertebrae and surrounding tissues with very minimal distortion caused by the discs 10. This is a significant improvement over the conventional metal discs which cause major distortion under MRI or CT imaging and tend to obliterate the surrounding structures by creation of artifacts that obliterate portions of the image.

With conventional metallic discs, the MRI and CT images are of little use in viewing the area surrounding the disc. Physicians are eager to have a MRI and CT scan friendly disc, such as those shown in the present application to allow them to diagnose continued pain which may or may not involve the disc. However, with conventional metallic discs it is often impossible to diagnose continued problems by available medical imaging techniques because of poor imaging.

One advantage of the two part PEEK plates 10, 12 with the metallic inserts is that the PEEK portion of the plates can be made to be removable without removal of the metallic insert. For example, in the event of excessive wear on the bearing surfaces of the plates 10, 12, the PEEK portion of the plates can be removed and replaced while leaving the metallic inserts 20 in place. Alternately, the PEEK portion of the plates 10, 12 can be removed while the metallic inserts remain and are incorporated in a subsequent fusion or other fixation procedure.

FIGS. 3-6 illustrate an alternative embodiment of a combination PEEK and metal disc having a two part metallic screen design. The disc (shown assembled in FIG. 5) includes an upper plate 110, a lower plate 112, and a core 114. The upper and lower plates 110, 112 are formed of a durable and imaging friendly material such a PAEK (PEEK) with an inner bearing surface for contacting the core 114 and one or more metallic inserts or screens 120A, 120B formed of a material which serves as a bone integration surface. As in the embodiment of FIG. 1, the inserts 120A, 120B may include one or more bone integration enhancing features such a serrations 118 and/or teeth or finlets 119 to ensure retention and bone integration. This disc construction differs from that of FIG. 1 in that the metallic screen 120A, 120B forms not only the bone integration surface having the serrations 118, but also includes a metallic fin 16 for better bone attachment to the fin.

The metallic screens are in the form of two part screens 120A and 120B formed of titanium by stamping, machining, or the like and secured together down a centerline by welding or other attachment. The two parts of the titanium screens 120A, 120B each include one half of a fin member 116 and one half of the opening 124 in the screens which accommodate a corresponding inner rim 122 of the PEEK plates 110, 112.

Figure 4:
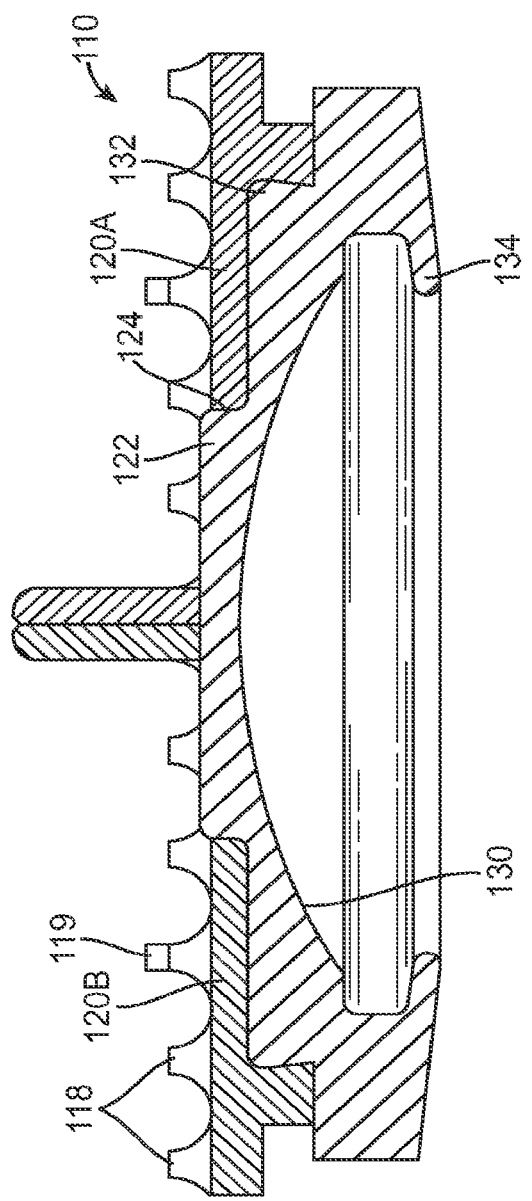
FIG. 4 is a cross sectional view of the plate of FIG. 3 taken along the line 4-4.
Figure 6:
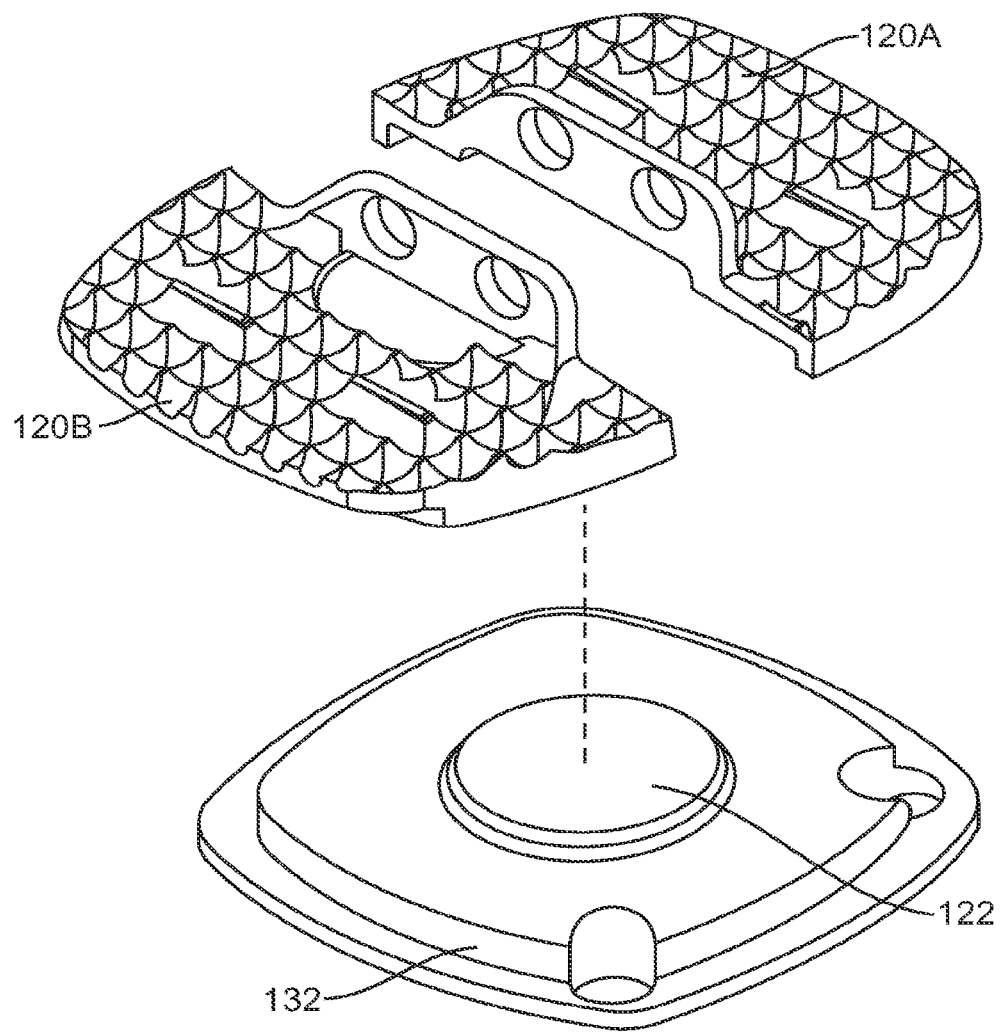
FIG. 6 is an exploded perspective view of the plate of FIG. 3.

FIGS. 4 and 6 illustrate the attachment of the two parts 120A and 120B of the metallic screen to the PEEK portion of the plate 110 by providing a peripheral protrusion 128 which surrounds and engages an outer rim 132 of the PEEK portion. This outer rim 132 has an angled outer surface which creates a locking fit when the two parts of the screen 120A, 120B are secured together. As in the embodiment of FIG. 1, the plate 110 includes a bearing surface 130 and can include a retention feature for retaining the core, such as the retaining ring 134. The screen 120A, 120B in this embodiment is preferably a thin screen having a thickness of about 0.5 mm to about 1.5 mm preferably about 0.5-0.1 mm not including a height of any serrations or teeth or the height of the peripheral protrusion 128.

Figure 5:
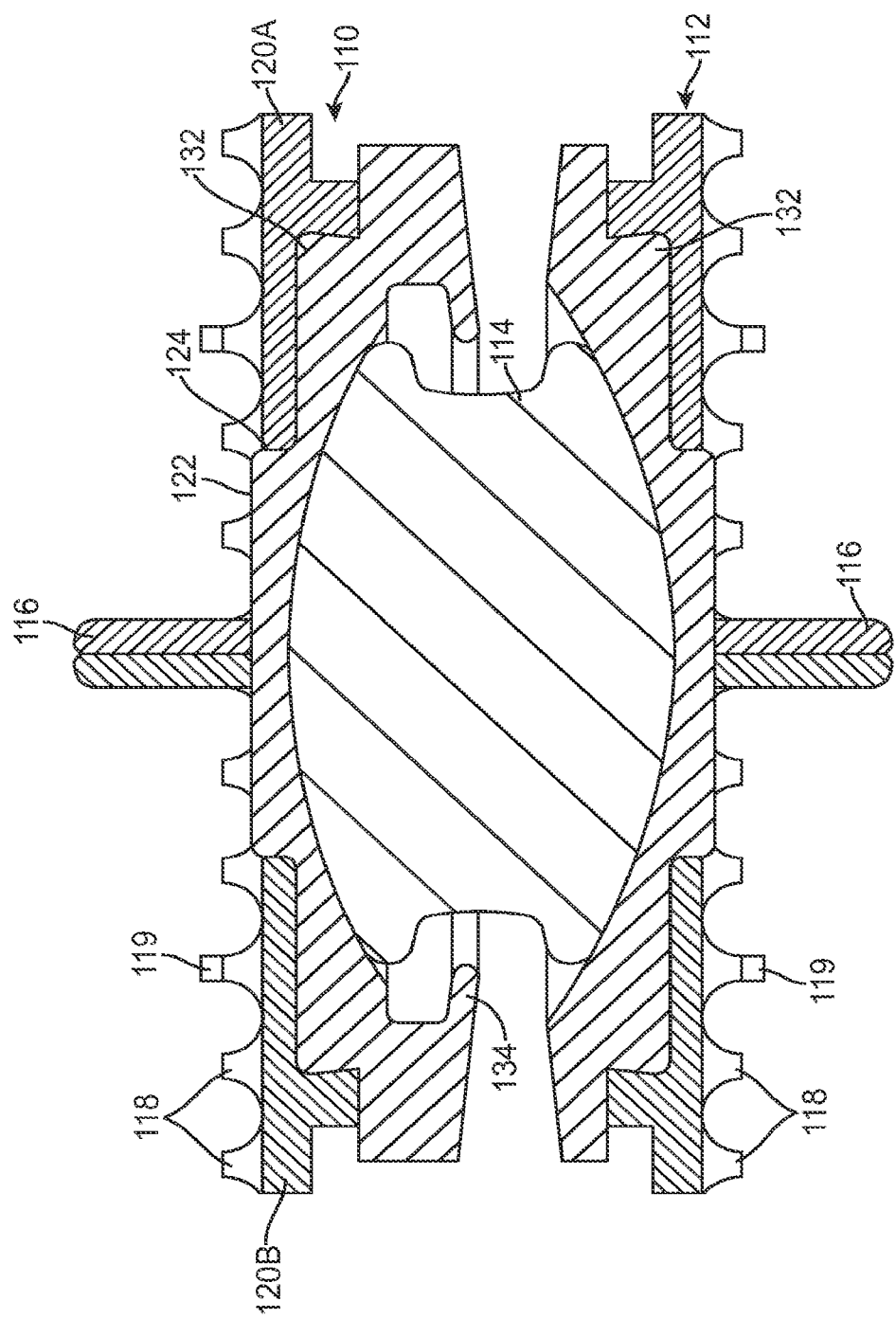
FIG. 5 is a cross sectional view of the assembled intervertebral disc including the plate of FIG. 4.
Figure 10:
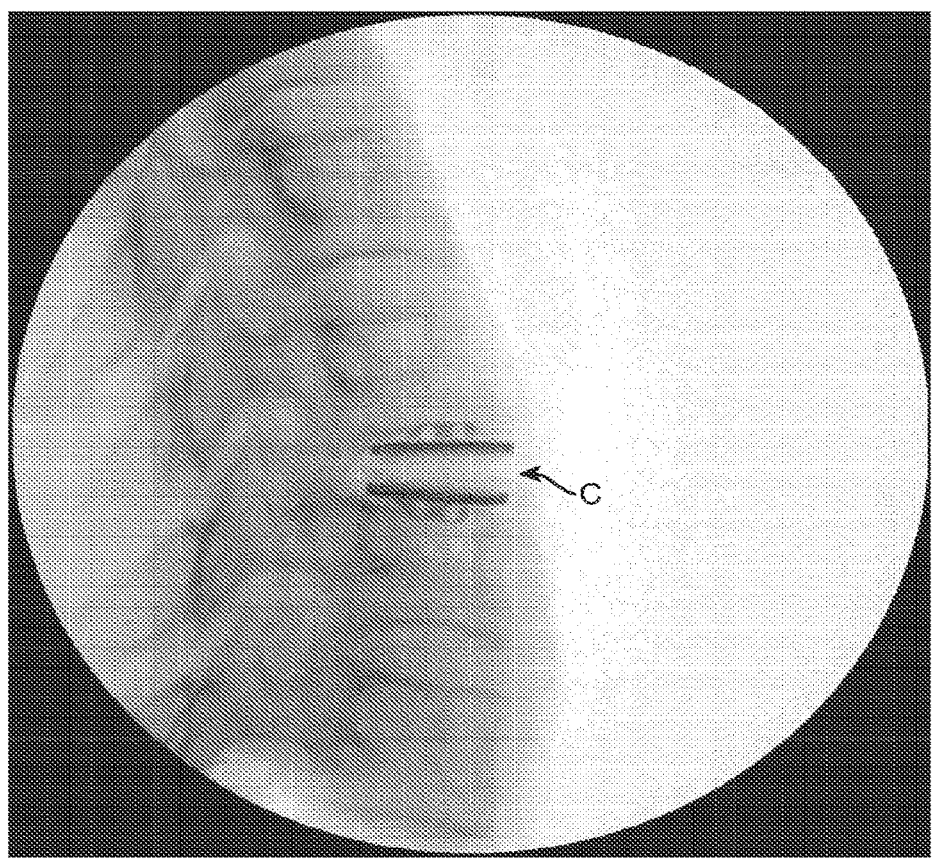
FIG. 10 is an X-ray image of one intervertebral disc according to the embodiment of FIG. 5 implanted in a spine.
Figure 11:
FIG. 11 is an MRI image of the intervertebral disc shown in the X-ray of FIG. 10.
Figure 12:
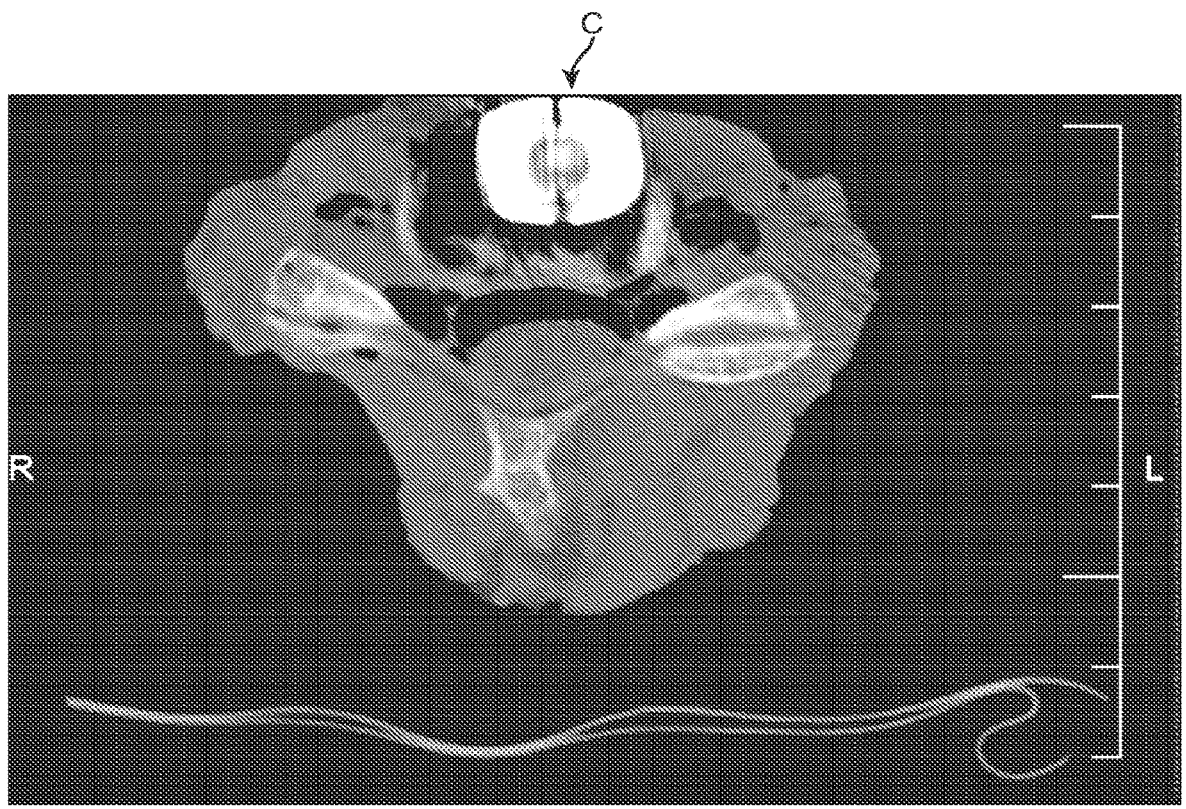
FIG. 12 is a CT image of the intervertebral disc shown in the X-ray of FIG. 10.

FIGS. 10-12 are images showing the intervertebral discs of FIG. 5 implanted in a cervical spine. The images are taken by X-ray (FIG. 10), MRI (FIG. 11) and CT scan (FIG. 12). The intervertebral disc is shown at C in the images and the metallic fins are visible on the plates. As can be seen particularly in the top view CT scan of FIG. 12, the spinal column is clearly visible without interference from the nearby disc.

In one embodiment of the invention, a PEEK core can incorporate one or more spring elements. The spring element can be formed of a metal material without concern of interaction of dissimilar metals. For example, a spring element formed of a nickel titanium alloy can be used between two PEEK end caps to form a compliant core in the manner described in U.S. patent application Ser. No. 12/358,716 filed Jan. 23, 2009, which is incorporated herein by reference in its entirety.

The combination PEEK and metal discs described herein can be used with many artificial disc designs and with different approaches to the intervertebral disc space including anterior, lateral, posterior and posterior lateral approaches. Although various embodiments of such an artificial disc are shown in the figures and described further herein, the general principles of these embodiments, namely providing a PEEK disc with a metallic insert for bone integration, may be applied to any of a number of other disc prostheses, such as but not limited to the LINK® SB CHARITE disc (provided by DePuy Spine, Inc.) MOBIDISK® (provided by LDR Medical (www.ldrmedical.fr)), the BRYAN Cervical Disc and MAVERICK Lumbar Disc (provided by Medtronic Sofamor Danek, Inc.), the PRODISC® or PRODISC-C® (from Synthes Stratec, Inc.), and the PCM disc (provided by Cervitech, Inc.).

In one alternative embodiment, the PEEK with metal screen disc is formed in a ball and socket design. In this embodiment the lower plate includes a lower surface with a titanium bone integration screen and an upper surface with a PEEK bearing surface in the form of a convex spherical surface. The upper plate includes an upper surface with a titanium bone integration screen and a lower surface with a PEEK concave bearing surface with mates with the concave bearing surface of the upper plate. This two piece PEEK and titanium disc can also take on other configurations with different shaped bearing surfaces, coated bearing surfaces and/or metallic bearing surface inserts.

Although the intervertebral discs described herein have been described primarily as including the combination of PEEK and titanium, it is understood that the disclosure of PEEK is intended to include other PAEK polymers and the disclosure of titanium is intended to include other biocompatible metals with good bone ongrowth properties.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A method for relieving back pain with an intervertebral disc capable of imaging under MRI, the method comprising:
   implanting an upper plate including a polyaryletherketone (PAEK) portion having a lower bearing surface and an upper anchoring element extending from an opposing side of the PAEK portion relative to the lower bearing surface, the upper plate further including an upper insert comprising an upper vertebra contacting surface positioned adjacent the PAEK portion and substantially surrounding the upper anchoring element, the upper vertebra contacting surface formed at least in part from a metal for improved bone attachment,
   wherein the upper insert is a separate component from the PAEK portion of the upper plate and when implanted, rests on the opposing side of the PAEK portion, and wherein the upper insert comprises an opening through which the anchoring element extends when implanted, the opening serving to locate the insert on the opposing side of the PAEK portion;
   implanting a lower plate including a polyaryletherketone (PAEK) portion having an upper bearing surface and a lower anchoring element extending from an opposing side of the PAEK portion relative to the upper bearing surface, the lower plate further including a lower insert comprising a lower vertebra contacting surface positioned adjacent the PAEK portion and substantially surrounding the lower anchoring element, the lower vertebra contacting surface formed at least in part from a metal for improved bone attachment,
   wherein the lower insert is a separate component from the PAEK portion of the lower plate and when implanted, rests on the opposing side of the PAEK portion relative to the upper bearing surface, and wherein the lower insert comprises an opening through which the lower anchoring element extends when implanted, the opening serving to locate the lower insert on the opposing side of the PAEK portion;
   positioning a solid one piece ceramic core between the upper and lower plates with the ceramic core having upper and lower ceramic bearing surfaces configured to mate with and articulate with respect to both the bearing surfaces of the upper and lower plates, wherein the core is the only member interfacing between the bearing surfaces of the upper and lower plates; and
   wherein upon imaging under X-ray the PAEK portion of the upper and lower plates are completely invisible and the upper and lower vertebral contacting surfaces of the upper and lower plates are completely visible.

2. The method of claim 1, wherein the core has an approximately symmetrical shape relative to a vertical axis of the intervertebral disc, wherein the upper and lower ceramic bearing surfaces have the same radius of curvature, wherein the core is movable with respect to the upper and lower plates.

3. The method of claim 2, wherein an MM image of the implanted upper and lower plates and core clearly show the vertebrae and surrounding tissues with very minimal distortion caused by the intervertebral disc.

4. The method of claim 1, wherein the upper anchoring element comprises a fin extending above the upper vertebra contacting surface of the upper plate as defined by the upper insert, wherein the opposing side of the PAEK portion of the upper plate comprises a rim that complements the opening in the upper insert to provide a snap lock feature for holding the upper insert in place relative to the PAEK portion of the upper plate after implanting,
   wherein the lower anchoring element comprises a fin extending below the lower vertebra contacting surface of the lower plate as defined by the lower insert, wherein the opposing side of the PAEK portion of the lower plate comprises a rim that complements the opening in the upper insert to provide a snap lock feature for holding the lower insert in place relative to the PAEK portion of the lower plate after implanting.

5. The method of claim 4, wherein the upper insert and the lower insert each comprise projections extending upward and downward, respectively, for improving bone attachment, and wherein the fin in the upper plate extends upward beyond the projections in the upper insert and the fin in the lower plate extends downward beyond the projections in the lower insert.

6. The method of claim 5, wherein the upper insert comprises a screen that ends before a posterior edge of the PAEK portion to allow improved imaging of a spinal column after the implanting of the upper plate and the lower plate and the positioning of the core.

7. The method of claim 6, wherein the fin in the upper plate and the fin in the lower plate each have an angled posterior end sized to enter a groove in adjacent vertebrae during the implanting of the upper plate and the lower plate, respectively.

8. The method of claim 1, wherein the upper insert and the lower insert are insert molded into the PAEK of the upper and lower plates, respectively.

9. The method of claim 1, wherein the upper insert and the lower insert each have a thickness of about 0.1 to about 1.0 mm.

10. The method of claim 1, further comprising removing at least one of the PAEK portion of the upper plate or the PAEK portion of the lower plate after the implanting processes without removing a corresponding one of the upper insert or the lower insert.

11. The method of claim 10, further comprising replacing the removed at least one of the PAEK portion of the upper plate or the PAEK portion of the lower plate after removal without removing the corresponding one of the upper insert or the lower insert.

12. The method of claim 1, wherein both the upper and lower bearing surfaces of the core are convex shaped.

13. A method of imaging a patient's spine with an artificial intervertebral disc, the method comprising:
   implanting an upper plate including a polyaryletherketone (PAEK) portion having a lower bearing surface and an upper anchoring element extending from an opposing side of the PAEK portion relative to the lower bearing surface, the upper plate further including an upper insert comprising an upper vertebra contacting surface positioned adjacent the PAEK portion and substantially surrounding the upper anchoring element, the upper vertebra contacting surface formed at least in part from a metal for improved bone attachment,
   wherein the upper insert is a separate component from the PAEK portion of the upper plate and when implanted, rests on the opposing side of the PAEK portion, and wherein the upper insert comprises an opening through which the anchoring element extends when implanted, the opening serving to locate the insert on the opposing side of the PAEK portion;
   implanting a lower plate including a polyaryletherketone (PAEK) portion having an upper bearing surface and a lower anchoring element extending from an opposing side of the PAEK portion relative to the upper bearing surface, the lower plate further including a lower insert comprising a lower vertebra contacting surface positioned adjacent the PAEK portion and substantially surrounding the lower anchoring element, the lower vertebra contacting surface formed at least in part from a metal for improved bone attachment,
   wherein the lower insert is a separate component from the PAEK portion of the lower plate and when implanted, rests on the opposing side of the PAEK portion relative to the upper bearing surface, and wherein the lower insert comprises an opening through which the lower anchoring element extends when implanted, the opening serving to locate the lower insert on the opposing side of the PAEK portion;
   positioning a rigid, one piece, ceramic core between the upper and lower plates with the ceramic core having upper and lower ceramic bearing surfaces configured to mate with and articulate with respect to both the bearing surfaces of the upper and lower plates, wherein the core is the only member interfacing between the bearing surfaces of the upper and lower plates; and
   imaging the implanted artificial disc with MIII, wherein the MM image of the implanted upper and lower plates and core clearly show the vertebrae and surrounding tissues with very minimal distortion caused by the intervertebral disc; and
   imaging the implanted artificial disc with X-ray, wherein the X-ray image shows the PAEK portion of the upper and lower plates are completely invisible and the metal upper and lower vertebral contacting surfaces of the upper and lower plates are completely visible.

14. The method of claim 13, wherein the core has an approximately symmetrical shape relative to a vertical axis of the intervertebral disc, wherein the upper and lower ceramic bearing surfaces have the same radius of curvature, wherein the core is movable with respect to the upper and lower plates.

15. The method of claim 13, wherein the upper anchoring element comprises a fin extending above the upper vertebra contacting surface of the upper plate as defined by the upper insert, wherein the opposing side of the PAEK portion of the upper plate comprises a rim that complements the opening in the upper insert to provide a snap lock feature for holding the upper insert in place relative to the PAEK portion of the upper plate after implanting,
   wherein the lower anchoring element comprises a fin extending below the lower vertebra contacting surface of the lower plate as defined by the lower insert, wherein the opposing side of the PAEK portion of the lower plate comprises a rim that complements the opening in the upper insert to provide a snap lock feature for holding the lower insert in place relative to the PAEK portion of the lower plate after implanting.

16. The method of claim 13, wherein the upper insert and the lower insert are insert molded into the PAEK of the upper and lower plates, respectively.

17. The method of claim 13, wherein the upper insert and the lower insert each a thickness of about 0.1 to about 1.0 mm.

18. The method of claim 13, wherein both the upper and lower bearing surfaces of the core are convex shaped.

* * * * *

UNITED STATES PATENT AND TRADEMARK OFFICE
CERTIFICATE OF CORRECTION

PATENT NO. : 11,207,190 B2  
APPLICATION NO. : 15/796086  
DATED : December 28, 2021  
INVENTOR(S) : Arramon et al.

Page 1 of 1

It is certified that error appears in the above-identified patent and that said Letters Patent is hereby corrected as shown below:

In the Claims

At Column 12, Line 36, in Claim 3, "The method of claim 2, wherein an MM image of the implanted upper..." should be -"The method of claim 2, wherein an MRI image of the implanted upper..."-

At Column 14, Lines 14 and 15, in Claim 13, "...imaging the implanted artificial disc with Mill, wherein the MM image of the implanted upper..." should be -"...imaging the implanted artificial disc with MRI, wherein the MRI image of the implanted upper..."-

Signed and Sealed this  
Third Day of May, 2022

Katherine Kelly Vidal  
*Director of the United States Patent and Trademark Office*